(12) United States Patent
Räsänen et al.

(10) Patent No.: US 6,795,178 B1
(45) Date of Patent: Sep. 21, 2004

(54) METHOD AND APPARATUS FOR ANALYSIS OF GAS COMPOSITIONS

(75) Inventors: Markku Räsänen, Helsinki (FI); Leonid Khriachtchev, Helsinki (FI); Mika Petterson, Vantaa (FI)

(73) Assignee: Helsinki University Licensing Ltd. Oy, Helsinki (FI)

( * ) Notice: Subject to any disclaimer, the term of this patent is extended or adjusted under 35 U.S.C. 154(b) by 0 days.

(21) Appl. No.: 09/647,458
(22) PCT Filed: Sep. 29, 2000
(86) PCT No.: PCT/FI99/00288
§ 371 (c)(1),
(2), (4) Date: Dec. 6, 2000
(87) PCT Pub. No.: WO99/51968
PCT Pub. Date: Oct. 14, 1999

(30) Foreign Application Priority Data

Apr. 3, 1998 (FI) ................................................. 980781

(51) Int. Cl.[7] ............................ G01J 3/30; G01N 21/25
(52) U.S. Cl. ........................ 356/311; 356/417; 356/419
(58) Field of Search ................................ 356/311, 313, 356/314, 316, 417, 419, 437

(56) References Cited

U.S. PATENT DOCUMENTS

| 4,848,138 A | 7/1989 | Marshall |
| 4,939,926 A | 7/1990 | Welch |
| 5,115,668 A | 5/1992 | Welch |
| 5,168,323 A | 12/1992 | Purtschert |
| 5,198,773 A | 3/1993 | Latta |
| 5,570,179 A | 10/1996 | Weckstrom |
| 5,920,400 A | * 7/1999 | Eisemann et al. .......... 356/425 |

FOREIGN PATENT DOCUMENTS

| DE | 3118060 | 11/1982 |
| GB | 1584612 | 2/1981 |
| WO | WO 9625658 | 8/1996 |

* cited by examiner

*Primary Examiner*—Alan Mathews
(74) *Attorney, Agent, or Firm*—Sughrue Mion, PLLC

(57) ABSTRACT

A non-invasive portable apparatus for analyzing the performance of gas-filled window glazing units is disclosed. The operation of the apparatus is based on discharging the spacing between the panels (2a, 2b) of the window glazing unit (1) by applying rapidly alternating electrical field to the spacing between the panels of the window glazing unit, on collecting and analyzing the emitted discharge light in different structural intervals. The discharge is created by a needle-like electrode (5), and the inner conducting layer (2a) of the glazing unit serves as another electrode. The localization of the discharge in the vicinity of the end of the needle-like electrode (5) makes it possible to collect the emitted light without routine adjustment of the optical system. In this case, factory-adjusted lenses (4a) can be used to collect the light from the discharge, and the collected light can be transported to light detectors (9a–9d) by using fiber optics (6), which eliminates influence of instability to the discharge geometry.

26 Claims, 2 Drawing Sheets

METHOD AND APPARATUS FOR ANALYSIS OF GAS COMPOSITIONS

This application is a 371 of PCT/F199/00288 filed Apr. 6, 1999.

BACKGROUND OF THE INVENTION

1. Field of the Invention

The present invention relates to spectroscopic analysis Of gas compositions in scaled containers. More specifically, the invention relates to a non-invasive method for selectively analysing gas-mixtures enclosed in a spacing betwee two glass sheets, such as between the panels of a window glazing unit. The present invention also concerns a modular, portable apparatus for analyzing the performace of gas-filled window glazing units.

2. Description of Related Art

Filling gases with low thermal conductivity, e.g. argon, krypton and xenon, as well as low emissivity coatings are used for a considerable reduction of heat transfer in window glazing units. The performance of the glazing units dranatically depends on the gas present in the spacing. For example, xenon and kryton provide mucb better insulation than argon. Also, as the rim seal is not perfectly leak tight, part of the filling gas can diffuse out and air can diffise into the spacing, resulting in dersing insulation performance. In order to predict the storage and opeuting lifetirnes, there is a need for precise analysis of the gas rnixture composition during manufacturing, storage and use. When the window fillings of existing constructions are to be tested, the movability of the measuring unit is of great importance.

Known gas analyzers employing mass-spectrometry and gas-chromatography are not suitable because they require physical contact with analyzed gas volume. Methods based on infrared and Raman spectroscopy are not applicable in the case of noble gas atoms because they essentially probe vibrational frequencies of molecules. Laser spectroscopic methods are not suitable because of complicated and expensive equipment employed. Direct measurements of the absorption spectra are also impossible to utilize in movable devices because the absorption lines of the noble gases occupy the vacuum ultraviolet spectral region not transmitted by the window glazing panels.

There are a number of known methods for spectroscopically analyzing the performance of gas-filled electronic lamps. In particular, a method utilizing optogalvanic phenomenon (U.S. Pat. No. 4,939,926) has been suggested for determining the performance of sealed rf discharged lamps at low pressure. The known method cannot be directly utilized for atmospheric pressure windows. In an embodiment described in the patent, a broad band ultraviolet-visible source is employed, which prevents the use of the method for selective measurements. In order for the optogalvanic approach to provide selectivity, a high-intensity tunable laser source should be used, which prevents the method from coming to portable realization.

DE Published Patent Application No. 195 05 104 discloses a method and an arrangement for testing the purity and pressure of gases for elctrical lamps. For the measurements both pressure dependent and independent emission lines are obtained. The prior art technology is designed for detection of impurities in electronic lamps, especially in those filled with noble gases. An external hf-excitation source with one electrode is used, and the lamp electrode acts as the other electrode. As regards the discharge excitation, the device is not suitable fbr atmospheric-pressure sealed containers because the measuremnet of argon pressure is insensitive when the pressure exceeds 10 kPa. Discharge in extensive volume requires high power of the source which means that portable realization is problematic A non-invasive pressure enasuring device described in US Pat. No 5,115,668 is used for estimating the luminance of an externally induced, high-frequency glow discharge of a gas in a lamp. Comparison of the measured luminance with calibrated luminance vs. pressure data provides the pressure for the gas. The device employs aan indirect method for pressure dependence of the luminance without any normalizing procedure, which makes it sensitive to geometrical re-arrangement so that the device is not really transportable. The method uses stable rf excitation and applies to a narrow field of application, i.e, low-pressure lamps, and it cannot be applied to atmospheric pressure sealed containers. The device measures the light in integral without wavelength analysis which means that it is not selective to different elements.

U.S. Pat. No. 5,570,179 discloses a measuring sensor and a measuring arrangement for use in the analysis of gas mixture, consisting of a chamber with transparent window (s) and arranged gas flow, two electrodes on the opposite side of the chamber to apply high alternating voltage to the gas flow, and light detector(s) to measure the intensity of radiation emitted through the chamber window in some selected spectral region. The device is designed mainly for surgical use in hospitals. The method is not non-invasive so that it is not applicable for sealed containers like gas-filled window glazing units. The use of two electrodes is impossible in a window units possessing an inner conducting layer.

There are a number of methods and devices specially created for estimating the performance of window glazing units. A known chemical gas monitor for detecting a leak of the window panel (cf. U.S. Pat. No. 4,848,138) uses chemicals, which are reactive with the constituents of air but not reactive with noble gases. The method requires special reconstruction of the window because the virtual chemical must be inserted during window manufacturing, and it cannot be used for existing constructions.

A known non-destructive method for determination of the rare-gas content of higly insulating glazing units (DE Published Patent Application No. 195 21 568.0) allows for the determination of the leak of air into the window spacing, at least, for krypton and xenon. The determination of the relative amount of the noble gas is based upon measuring the sound velocity in the gas filling. The method is, however, mainly applicable to stationary measurements because it requires precise control of measurement condition (tenperature, spacing distantce, etc.), which makes any portable realization very questionable and field measurements impossible. Also, the method is inselective to argon filling, which is the most important in the area. The method is inselective to different noble gases so that it is unable to distinguish, for example, a mixture of krypton with air from proper filling with argon.

To complete the survey of related art, a method of determining the percentage gas content of an insulating glass window unit is known from U.S. Pat. No. 5,198,773. The prior method is based on applying a voltage to opposite panes of the unit, progressively increasing the voltage, monitoring the voltage, recording the value of threshold discharge voltage, and converting the magnitude to perentage gas content between the panes. The method is directed to recognizing the percentage content of some given gas (e.g. argon or sulfur hexafluoride) between gas panel, and it is impossible to apply it for a window unit of unknown filling. In other words, the prior method is not selective to different noble gas fillings. Also, the necessary use of two electrodes prevents the method from measuring units with conducting inner layers, which are commonly used now to improve insulation performance of the production.

SUMMARY OF THE INVENTION

It is an object of this invention to eliminate the problems relating to the pior art and to provide a novel method for selectivc identification of gas components present in a gas or gas mixture.

It is another object of the invention to provide a compact, easily movable and inexpensive device, which is suitable for selective identification of gas components typical for insulation window glazing units, i.e., argon, krypton, xenon and air.

These and other objects, together with the advantages thereof over known processes, which shall become apparent fiom specification which follows, are accomplished by the invention as hereinafter described and claimed.

The present invention is based on the concept of discharging the spacing between the panels of the window glazing unit by applying rapidly alternating electrical field to the spacing between the panels of the window glazing unit. To achieve a discharge, a grounded counter-eclectrode is used. In particular, the present invention comprises creating a local excitation of the gas in a glazing unit by using an electrode, while the inner conducting layer of the glaizng unit may serve as the counter-electrode. The emitted light of the discharge is collected from a collection area larger than the emission area, analyzed in different spectral intcrvals and the concentration of a gas of interest is calculated by comparing the intensity of a spectral interval corresponding to said gas with the intensity of another interval.

The localization of the discharge in the vicinity of the end of an electrode having a small end (e.g. a needle-like electrode) allows for collection of the emitted light without routine adjustment of the optical system.

According to the present invention, the apparatus for non-invasive analysis of, e.g., gas-filled window glazing units comprises means for locally applying the rapidly alternating high voltage to the spacing of the window glazing unit to achieve local emission and means for collecting and transporting emitted light. Further, there are means for determining the intensity of at least two different spectral intervals, at least one of which corresponds to the gas component of interest, and means for calculating the ratio between the intensities of the different spectral intervals.

More speciffically, the non-invasive method according to invention is mainly charaterized by what is stated in the characterizing parts of claims 1 and 10.

The apparatus according to the invention is characterized by what is stated in the chargacterizing part of claim 11.

Considerable advantages are achieved by the invention. Thus, factory-adjust lenses can be used to collect the light from the discharge, and the collected light can be transported to light detectors by using fiber optics, which eliminates influence of instability of the discharge geometry.

According to a preferred embodiment, a maodular apparatus is provided, in which the elcetrode used for local application of rapidly alternating high voltage to the spacing of the window glazing unit and the lens or mirror used for collecting the emitted light are arranged in one portable unit (remote sensor unit) which easily can be tratsported to the vicinity of the glazing unit which is to be tested. The remaining part of the apparatus can be mounted into a, likewise movable, separate processing unit. If desired, the remote sensor unit can further be provided with means for displaying the obtained information about the performace of the window glazing unit, so as to provide the person testing the window to obtain the necessary data for evaluating the performance of the window. An additional light detector can also be fined in the remote sensor unit and connected to the processing means with an additional electrical line, a high alternating voltage being automatically applied to a sample container in absence of a discharge through the window glazing unit.

The movability of the device means that it is possible to use it in field to analyze gas components inside window units installed in real buildings, not only during the manufacturing of window glazing units. The selectivity of the device to the gas components means that it distinguishes between the components without information about the gas filling obtained a priori. The device probes the gas components at normal atmospheric pressure. In order to estimate the operation quality of the window units, the device is capable of recognzing a window unit with more than a specified concentration (e.g. 10%) of air in addition to a filed noble gas. For determining the performance of the window unit, the device is further capable of discriminating between different possible noble gases (argon, krypton, xenon). In other words, the device is capable of analyzing the gas composition whlen the gases are argon, krypton, xenon, and air.

Next the invention will be examined in more closely with the aid of a detailed description with reference to the attached drawings.

DETAILED DESCRIPTION OF THE INVENTION

Figure 1:
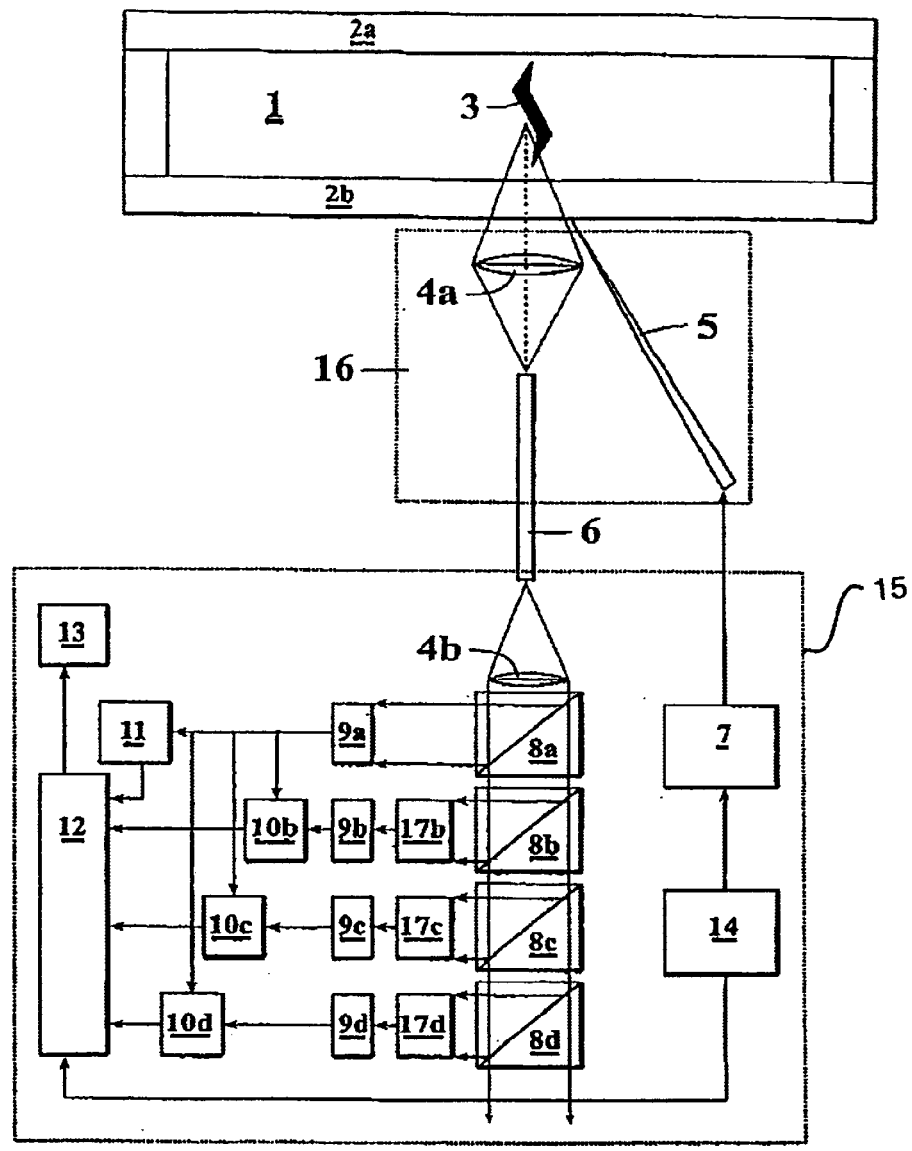
FIG. 1 is a schematic illustration of one embodiment of the non-invasive device for analyzing the performance of gas filled window glaing units.

The following description will examine the invention when used in connection of a gas-filled window glazing unit. It should be pointed out that the invention is, however, more generally applicable to any closed spacings having at least one wall of a transparnt or even translucent material. It is required that the material has dielectric properties (rather than conducting properties) to allow for the creation of a discharge by high voltage. Further it is required that the transparent or trauslucent material allows for transmission of enough emitted light to make spectral recognition possible.

The operation of the non-invasive device according to the present invention is based on discharging the spacing betwee the window panels of a glazing unit by applying rapidly alternating electrical field, collecting and analyzing the emitted light in different spectral intervals in comparison with another spectral inverval or with the integral value of the emittance. Rapidly alternating electrical field is known to produce mainly excitation of neutral particles, and ionization as well as dissociation are of minor importance. In discharge, the excited atoms and molecules emit light which is collected and analyzed.

The spectral properties of the emitted light reflect the gas composition in the discharged spacing. In particular, there are a number of known characteristic lines for different elements, and they can be chosen, for example, as 812 nm for argon 587 nm for krypton, and 467 nm for xenon. These characteristics lines are well seperated from each other so that they can be selected by ordinary interference filters. Molecular species, which are specific for air, emit vibrationaly structured spectrum in much broader spectral interval, and they provide mainly enittance signal in integral when no spectral selection is used. These dramatic spectral differences in emission of the species of interest construct the fundamental basis for the invention. By comparing the intensities emitted in different spectral intervals with the the intensity of another spectral interval or with the integral intensity the gas conposition in the discharg volume cam be extracted.

The present device can be calibrated by creating a correlation between the discharge spectra and gas-mixture concentration. The concentration inside a sample window unit can be prepared using, e.g. a multi-channel gas-flow meter. Correlation curves, such as those shown in FIGS. 2a and 2b, can be obtained as explained in connection with the Example below. Thus, in the present method, the spectrum of the discharge is measured to obtain numerical parameters, and then the gas mixture concentration can be determined from a calibration curve.

In order to create the discharge, two electrodes, an internal (conducting layer of the window glazing unit), and external are used. As mentioned above, it is also possible to use a second external electrode as a counter electrode should the glazing unit not be provided with a conducting layer. An important feature of the invention comprises localization of the discharge, which is achieved by employing an electrode having a small area at least in two dimensions. Examples of such electrodes are electrodes having an elongated body with a tapered end. The size of the end is preferably less than 10 mm, in particular about 1 mm in diameter. Other examples are conductive layers having a cormesponding small area. Such conductive layers can be deposited on the surface of the lens used for collecting the emissions. In this case, the discharge starts in the vicinity of the end of the electrode. This localization allows reliable collecting the emitted light to be provided without routine adjustment of the optical system. In the present invention, microlenses can be used to collect the light from the discharge, and the collected light can be transported to light detectors by using fiber optics. It is important that spliting the light to differet beams is done after the optical fiber but not from the discharge, which eliminates any influence of natural instability of the discharge geometry.

The processing of the spectral data obtained will be dealt with more closely in rclation to the practical embodiment of FIG. 1.

Within the scope of the present invention, the term "local" or "localized" discharge means that the discharge takes place in only a part of the closed spacing of interest. As a practical matter, the localized discharge means that the collection of the emission is carried out from a collecting area larger than the emission area.

The above embodiment describes using the integral intensity of the emiasion for determining the concentration of a gas component of interest by forming the ratio of the intensity of a spectral interval corresponding to the gas component and the integral intensity. It should, however, be pointed out that the intensity of a spectral interval corresponding to another gas component or the intensity of a different spectral interval corresponding to the same gas component can be used for the same purpose. Thus, the method according to the present invention comprises the alternative of determining the intensity of a first speciral interval corresponding to the gas component of interest and the intensity of a second spectral interval, different from the first spectral interval, said second spectral interval corresponding to the integral emission, to the emission of another component of the gas mixture, or the emission of the same gas component.

Turning now to the embodiment depicted in FIG. 1, it can be noted that the gas mixture 1 to be analyzed is kept inside the window glazing unit. The window glazing unit particularly contains two glazing panels 2a and 2b. The internal surface of one of the panels, specically 2a, is covered by the layer, which conducts electrical current, and the other panel (2b) is free of conducig coating.

The non-invasive device depicted in the drawing for analyzing the performnance of iu gas-filled window glazing units comprises a needle-like electrode 5 for applying rapidly alternating high voltage to the spacing of the window glazing unit, a lens 4a for collecting the eniitted light, and an optical fiber 6 for transporting the collected light. These parts of the device can be fitted into a fast module, which can be called a remote sensor unit 16. The device further comprises a processing unit (or measuring and displaying unit) 15 with a lens 4b for collimating the transported light, beam splitters 8a, 8b, 8c and 8d for splitting the collimated light beam, one normalizing light detector 9a for measuring a signal proportional to the integr discharge emittancc, Iaee component light detectors 9b, 9c and 9d with means 17b, 17c and 17d for spectral selection of diffget characteristc lines of gas components, data processing means 10b, 10c and 10d for comparing signals in the different channels to estimate gas composition in the window glazing unit, a processor 12, means 11 for detecting the existence of the discharge, means 13 for displaying the obtained infoxmation, means 7 for creating a rapidly alternating high voltage, and a switcher 14.

The apparatus is operated as follows. Rapidly alternating electrical field is applied to the window glazig unit from the side of the panel 2b by using the needle-like electrode 5. As the other electrode, the conducting layer of the panel 2a is used. The rapidly alternating electrical field produces a discharged channel in the spacing between the glazing panels, and the discharge starts in the close vicinity to the end of the electrode 5. Emitted light is collected by a lens 4a. The end of the electrode 5 is located at about 0.5 to 3, preferably about two focal distances of the lens 4a from the lens 4a. The collected light is directed into the optical fiber 6, the end "a" of which locates at about two focal distances from the lens 4a and about at a discharge-lens axis.

The light, transmitted by the optical fiber 6 and emitted from the end "b" of the optical fiber 6, is then collimated by a lens 4b. The lens 4b is located at about 0.5 to 2, preferably about one focal distarce from the end "b" of the optical fiber 6. Quasi-parallel light beam goes through a sequence of four beam splitters 8a, 8b, 8c, and 8d. Deflected beams are drected onto light detectors 9a, 9b, 9c, and 9d. The light detector 9a measures intensity proportional to the integral intensity of the discharge. The light beams directed to light detectors 9b, 9c, and 9d are specturally selected by spectral filters 17b, 17c, and 17d to measure signals proportional to gas component percentage. The electrical signal from the light detector 9a is applied to comparing units 10b, 10c and 10d to generate ratios of the spectally selected and integral signals. Also, the electrical signal fromn the light detector 9a is applied to a level unit "Yes-No" 11 to check the appearance of the electrical discharge 3 in the spacing of the window glazing unit. Electrical signals from the level unit "Yes-No" 11 end from the comparing units 10b, 10c and 10d are applied to a processor 12 to be analyzed. The result of the analysis by the processor 12 is shown at a display 13. In particular, the following information is to be displayed: existence of the discharge, type of dominating filling (argon, krypton, xenon), percentage of the dominating filling. The alteating high voltage to apply to the electrode 5 is created by a high-voltage generator 7. The operation of the device is started and stopped by a switcher 14.

Although not shown in FIG. 1, the measurng and displaying unit 15 is electrically supplied either from the electrical network or from a battery. The light detectors 9a, 9b, 9c, and 9d include corresponding pre-arnplifiers (not depicted) to construct proper electrical signals.

In addition to the numerous advantages of the invention explained above it should be pointed out in connection with the practical embodiment of FIG. 1 that it removes the need for calibration of absolute luminescence flux because the device analyzes the ratios between fluxes in spectral interval with normalization by integral flux. Another important feature of the present embodiment is that there is no need in geometrical stability of the measurement base the device analyzes the ratios between fluxes in spectral interval with normalization by integral flux, and optical alignment with required accuracy is prepared at the manufacturing stage. Practically, this means the opportunity of movable performance of the device.

It is understood that many changes and additional modifications are possible in view of different versions of performance without departing from the scope of the inventions as defined in the appended claims. Thus, as explained in connection with the method, the means (9a) for measuring a signal proportional to the integral discharge ermttance can be replaced with menns for measuring a signal proportional to any spectral interval useful for the determination of the gas concentration of the gas of interest. A combination of the features of the claims produces additional advantages.

In particular, it is also possible to mount the means for displaying the obtained information about performance of the window glazing unit in the remote sensor unit formed by the means for locally applying rapidly alternating high voltage and the lens.

The means for measuring gas component signals can comprise a CCD camera.

As briefly discsed above, the apparatus can also contain a sample container for controliing the operational performance of the apparatus as a whole. The sample container is preferably installed into the remote sensor, which is provided with an additional light detector and connected with the data processing means, whereby the apparatus can be operated so that a high alternating voltage is autornatically applied to the sample container in the absence of a discharge through the window glazing unit.

The means for splitting the collimated beam and spectrally selecting the charactenstic lines can comprise a spectrometer.

EXAMPLE

A window-glazing unit with a spacing between the window frames of 12 mm and having a conductive selecive coating on one side of the window was used for establishing a numerical correlation between emission from discharged air-Ar mixture and the relative gas concentration. The window was provided by VTT (Espoo, Finland) and it is similar to units manufactured in industry. The window spacing was flushed with an atmospheric-pressure pressure mixture of Ar and synthetic air in well-defined proportions as measured by a gas-flow meter (Brooks, M+05850S). The spacing was discharged fromn the non-coated side by a Tesla generator. A plastic fiber optics (1 mm of thickness) transported the emission light to a spectrometer (Ocean Optics S2000, 1 nm of resolution) controlled by a portable computer. Basically, the experimental procedure corresponded to the scheme described. above in connection with FIG. 1. The discharged light collected by lens 4a transported through optical fiber 6 was conducted to the entrance or input channel of a spectrometer S2000 equipped with a CCD detector. The spectrometer with the CCD detector resembles the elements 8 (beam splitter), 9 (detector) and 17 (filters) disclosed in FIG. 1. The signals from the CCD detector were analyzed by a computer, which gave functions 10 (comparing units), 11 (level unit), 12 (processing) and 13 (displaying).

The device was calibrated by crating a correlation betwin the discharge spectra and gas-mixture concentration.

It was found that a discharge through the window spacing was present for a 0 to 50%. range of relative concentration of air in the mixture, and the resulting emission spectra essntially depended on the Ar-air concentration ratio. When the relative conentration of air is small, the argon lines in the 690 to 800 nm region dominate in the spectrum. When the amount of air increases, emission lines fom air grow occupying UV-visible region of the spectrum.

Figure 2A:
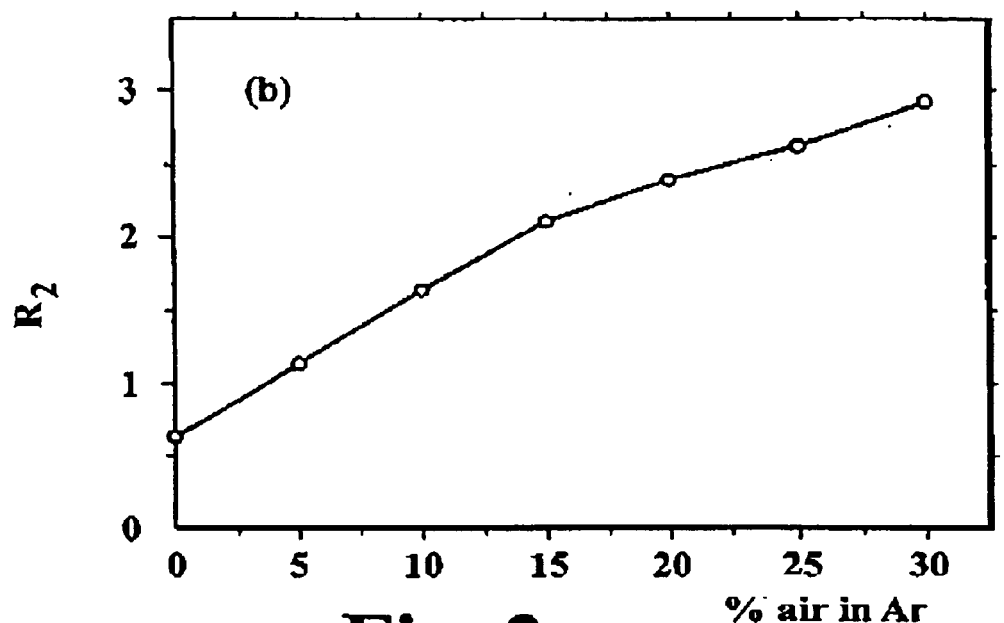
FIG. 2a presents the correlation bewd the amount of air in the window and the intensity ratio $R_1 = I(402–408)/I(694–699)$.
Figure 2B:
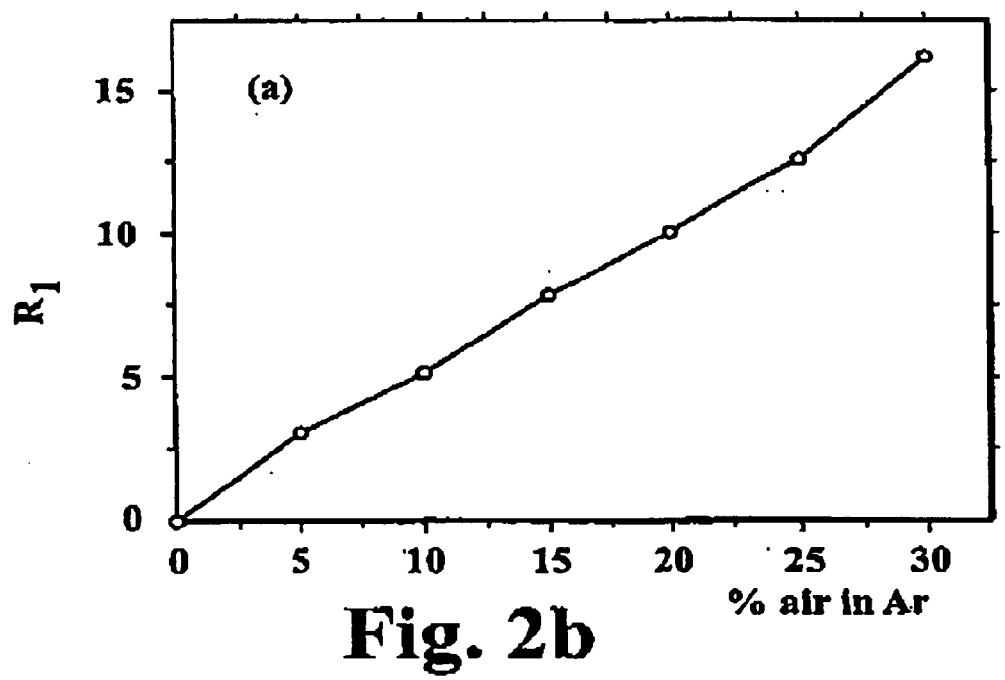
FIG. 2b displays the aicneenttion dependence of the parameter $R_2 = I(748–753)/I(694–699)$ employing Ar lines only where the numbers in parenthesis denote the spectral interval in nanometers.

By normalizing the sigas from air and Ar against integrate intensity it is possible to obtain empirical parameters connecting the relative concentrations with the shape of the measured spectra. Similar correlation curves can be obtained by comparing the ratio between line intensities of air and Ar with the relative concentrations. FIG. 2(a) presents such a correlation between the amount of air in the window and the intensity ratio $R_1 = I(402-408)/I(694-699)$ where numbers in parentheses give the integration interval in nanometers, the first intensity belonging to air and the second one originating from Ar emission. It is seen that the correlation unction is straightforward and nearly linear.

Additionally, it appeared that the spectnm of Ar emission itself shows repeatable modifications when the amount of air changes. This effect arises from differences in properties of the emitting Ar levels (energy, lifetime, etc.), which influences partial energy flows from different Ar levels to air buffer. The air-concentration dependence of the parameter $R_2 = I(748-753)/I(694-699)$ employing Ar lines only is displayed in FIG. 2(b).

Thus, the correlation caves presented in FIG. 2 allow for accurate extraction of relative Ar-air concentration from the discharge emission measured. An analysis shows that the accuracy of the estimate is better than 1% in absolute concentration in the practically important region from 0 to 30% of relative air concentration with the intention time below 1 sec. and both parameters $R_1$ and $R_2$ yield similar accuracy in this region. In the region from 30% to 50% of relative air concentration, the absolute accuracy decreased.

Also the correlation functions were tested for different positions of the optical fiber and various discharge voltages (three different Tesla generators) and they were shown to be practically independent of these parameters. Also, the method was successfully tested for Kr-air mixtures.

What is claimed is:

1. A non-invasive method for selectively determining the concentration of at least a first gas component in a gas mixture contained in a closed spacing (1) having at least one transparent, dielectric wall (2a, 2b), comprising:

locally applying rapidly alternating high voltage to the spacing to provide localized light emission (3) in an emission area;

collecting emitted light of the local emission (3) from a collection area larger than the emission area;

determining the intensity of at least two different spectral intervals, at least one of which corresponds to the gas component of interest;

calculating the ratio between the intensities of two spectral intervals, one of which corresponds to the gas component of interest; and determining the concentration of the gas component of interest from said ratio, wherein determining the intensity comprises: determining the intensity of a first spectral interval correspondinp to the gas component of interest and the intensity of a second spectral interval, different from the first spectral interval, said second spectral interval corresponding to the integral emission, to the emissions of a second component of the gas mixture, or the emission of the said first gas component.

2. The method according to claim 1, wherein the spacing (1) comprises two glass walls formed by two glass sheets (2a, 2b) spaced apart from each other.

3. The method according to claim 2, wherein the spacing comprises a gas-filled window glazing unit (1).

4. The method according to claim 1, wherein a grounded counter-electrode is used.

5. The method according to claim 1, wherein alternating high voltage is applied to the closed spacing using an elongated electrode (5) having a tapered end and by directing said end of the electrode against the closed spacing.

6. The method according to claim 1, wherein the light of the local emission is collected with a lens (4a) to provide a collimated light beam, said lens being located at a distance of about 0.5 to 3 focal distances from the site of the local emission.

7. The method according to claim 6, wherein the collimated light beam is split to provide a first split beam having a signal proportional to the integral discharge emittance and a second beam which is used for measuring a signal dependent on the concentration of one gas component, said split signals being subjected to spectral filtration to measure signals dependent on specific gas components.

8. The method according to claim 7, wherein the collimated light beam is split to provide at least one further split signal used for measuring signals proportional to the concentration of at least one further gas component.

9. An apparatus for non-invasive analysis of gas-filled window glazing units (1) for determining the performance thereof, comprising:

means (7) for creating rapidly alternating high voltage, means (5) for locally applying the rapidly alternating high voltage to the spacing of the window glazing unit to achieve local emission;

means (4a, 6, 4b) for collecting and transporting emitted light;

means (9a to 9d) for determining the intensities of at least two different spectral intervals, at least one of which corresponds to the gas component of interest;

means (10b–10d) for calculating the ratio between the intensities of two spectral intervals, one of which corresponds to the gas component of interest; and means (12) for determining the concentration of the gas component from said ratio, wherein the means for collecting and transporting the emitted light comprise a collecting lens (4a) which can be brought in the vicinity of the closed spacing, wherein the means (5) for locally applying ratidly alternating high voltage and the lens (4a) are fitted together to form a separate sensor unit.

10. The apparatus according to claim 9, wherein the means for locally applying rapidly alternating high voltage comprise a needle-like electrode (5).

11. The apparatus according to claim 9, wherein the means for locally applying rapidly alternating high voltage comprise a conductive layer coated on the means for collecting the emitted light, which can be used as an electrode.

12. The apparatus according to claim 9, wherein the apparatus contains a second electrode, which can be grounded and set on the opposite side of the window unit.

13. The apparatus according to claim 9, wherein the means for collecting and transporting the emitted light further comprise optical fibres (6) for transporting the light and a collimating lens (4b) for collimating the light transported by the optical fibres.

14. The apparatus according to claim 13, wherein the optical fiber (6) comprises optical connectors for connecting to the collecting lens (4a), to the collimating lens (4b) and/or to another optical fiber.

15. The apparatus according to claim 9, wherein the means for collecting and transporting the emitted light (4a, 6, 4b) are formed as a single non-adjustable block (16).

16. The apparatus according to claim 9, comprising means (8a–8d) for splitting the collimated light into a first splitted beam having a signal proportional to the integral discharge emittance and at least one second beam for measuring a signal proportional to the concentration of one gas component.

17. The apparatus according to claim 9, wherein the means for determining the intensity of the spectral interval corresponding to the gas component of interest comprise light detectors (9b–9d) with means (17b–17d) for spectral selection of different characteristic lines of gas components.

18. The apparatus according to claim 17, wherein the means for spectral selection comprise interference filters (17b–17d).

19. The apparatus according to claim 18, wherein the interference filters (17b–17d) have central wave lengths at 467 nm, 587 nm and/or 812 nm.

20. The apparatus according to claim 17, wherein the means for measuring gas component signals are performed as a CCD camera.

21. The apparatus according to claim 9, wherein the apparatus contains a sample container for controlling the operational performance of the apparatus as a whole.

22. The apparatus according to claim 9, further comprising:

data processing means (12) for comparing signals in order to estimate gas composition in the window glazing unit; and means (13) for displaying the obtained information.

23. The apparatus according to claim 22, further comprising means for collimating the transported emitted light, to produce a collimated beam and means for splitting the collimated beam and wherein the means for determining the intensities of at least two different spectral intervals includes means for spectrally selecting different characteristic lines of gas components, and wherein the means for splitting and means for spectrally selecting the characteristic lines comprise a spectrometer.

24. The apparatus according to claim 23, further comprising means (13) for displaying obtained information about a performance of the window glazing unit, said means for displaying being is mounted in the separate sensor unit (16) formed by the means for locally applying rapidly alternating high voltage and the lens.

25. The apparatus according to claim 24, wherein a sample container is installed into a remote sensor (4a, 6, 4b), which is provided with an additional light detector and connected with the data processing means (12), whereby the apparatus can be operated so that a high alternating voltage is automatically applied to the sample container in the absence of a discharge through the window glazing unit.

26. The apparatus according to claim 9, comprising means (9a) for determining the integral intensity of the emission and means (9b–9d) for determining the intensity of at least one spectral interval corresponding to the gas component of interest.

* * * * *